US011529060B2

(12) United States Patent
Hermeling et al.

(10) Patent No.: US 11,529,060 B2
(45) Date of Patent: Dec. 20, 2022

(54) METHOD FOR DETERMINING TIME DELAY BETWEEN BEAT-TO-BEAT BLOOD PRESSURE SIGNAL AND PULSE ARRIVAL TIME

(71) Applicant: Samsung Electronics Co., Ltd., Suwon-si (KR)

(72) Inventors: Evelien Hermeling, Eindhoven (NL); Eva Wentink, Eindhoven (NL)

(73) Assignee: Samsung Display Co., Ltd.

( * ) Notice: Subject to any disclaimer, the term of this patent is extended or adjusted under 35 U.S.C. 154(b) by 622 days.

(21) Appl. No.: 16/530,919

(22) Filed: Aug. 2, 2019

(65) Prior Publication Data
US 2020/0315470 A1   Oct. 8, 2020

Related U.S. Application Data

(60) Provisional application No. 62/830,224, filed on Apr. 5, 2019.

(51) Int. Cl.
| | | |
|---|---|---|
| *A61B 5/021* | (2006.01) | |
| *A61B 5/0205* | (2006.01) | |
| *A61B 5/024* | (2006.01) | |
| *A61B 5/02* | (2006.01) | |
| *A61B 5/022* | (2006.01) | |
| *A61B 5/318* | (2021.01) | |

(52) U.S. Cl.
CPC ........ *A61B 5/02125* (2013.01); *A61B 5/0205* (2013.01); *A61B 5/02416* (2013.01); *A61B 5/022* (2013.01); *A61B 5/02028* (2013.01); *A61B 5/318* (2021.01)

(58) Field of Classification Search
CPC .............. A61B 5/02125; A61B 5/0205; A61B 5/02416; A61B 5/318; A61B 5/02028; A61B 5/022; A61B 5/352; A61B 5/02108; A61B 5/7275; A61B 5/725; A61B 5/7203; A61B 5/7285
See application file for complete search history.

(56) References Cited

U.S. PATENT DOCUMENTS

| | | |
|---|---|---|
| 6,120,459 A | 9/2000 | Nitzan et al. |
| 7,029,447 B2 | 4/2006 | Rantala |
| | (Continued) | |

*Primary Examiner* — Gary Jackson
*Assistant Examiner* — Sebastian X Lukjan
(74) *Attorney, Agent, or Firm* — Innovation Counsel LLP

(57) ABSTRACT

A method for providing personalized health assessment of a subject includes: receiving a raw electrocardiography (ECG) signal of a subject from an ECG device and a raw blood pressure (BP) signal of the subject from a BP waveform detector; calculating a beat-to-beat ECG signal from the raw ECG signal; calculating a beat-to-beat BP signal from the raw BP signal; calculating a beat-to-beat pulse arrival time (PAT) signal that is measured as a time delay between the beat-to-beat ECG signal and the beat-to-beat BP signal; calculating an interpolated beat-to-beat PAT signal and an interpolated beat-to-beat BP signal by interpolating the beat-to-beat PAT signal and the beat-to-beat BP signal, respectively; assessing a subject-specific relationship between the interpolated beat-to-beat PAT signal and the interpolated beat-to-beat BP signal; and estimating a real-time blood pressure of the subject based on the subject-specific relationship.

20 Claims, 7 Drawing Sheets

(56) References Cited

U.S. PATENT DOCUMENTS

| | | | |
|---|---|---|---|
| 10,786,161 B1* | 9/2020 | Archdeacon | A61B 5/7278 |
| 2011/0009755 A1* | 1/2011 | Wenzel | A61N 1/36585 |
| | | | 600/485 |
| 2011/0021929 A1 | 1/2011 | Sethi et al. | |
| 2011/0144456 A1 | 6/2011 | Muhlsteff et al. | |
| 2012/0203077 A1* | 8/2012 | He | A61B 5/6815 |
| | | | 600/301 |
| 2016/0143546 A1 | 5/2016 | McCombie et al. | |
| 2016/0302677 A1* | 10/2016 | He | A61B 5/02125 |
| 2016/0331328 A1* | 11/2016 | Looney | A61B 5/6843 |
| 2017/0079533 A1* | 3/2017 | Robinson | A61B 5/0075 |
| 2017/0347899 A1* | 12/2017 | Bhushan | A61B 5/02055 |
| 2018/0289288 A1* | 10/2018 | Kim | A61B 5/1102 |

* cited by examiner

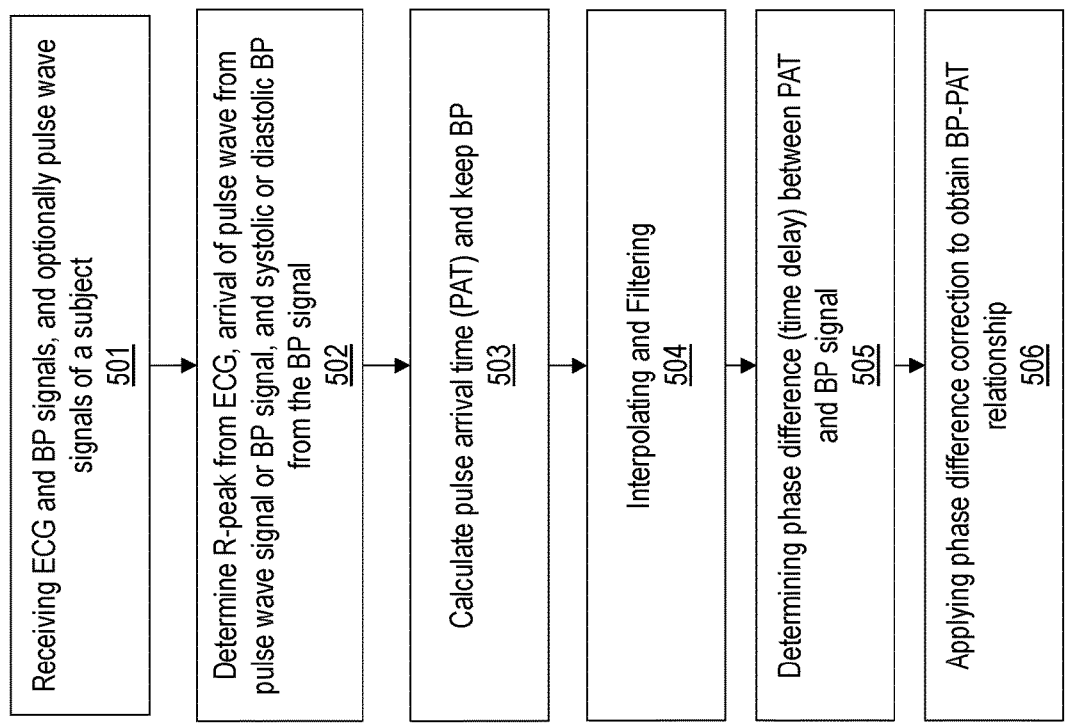

METHOD FOR DETERMINING TIME DELAY BETWEEN BEAT-TO-BEAT BLOOD PRESSURE SIGNAL AND PULSE ARRIVAL TIME

CROSS-REFERENCE TO RELATED APPLICATION(S)

This application claims the benefits of and priority to U.S. Provisional Patent Application Ser. No. 62/830,224 filed Apr. 5, 2019, the disclosure of which is incorporated herein by reference in its entirety.

TECHNICAL FIELD

The present disclosure relates generally to a health monitoring system and method, more particularly, to a system and method for accurately assessing personalized subject-specific relationship between a blood pressure and a pulse arrival time.

BACKGROUND

Electrocardiography (ECG) is an electrophysiological monitoring technique to detect electrical activities of a human heart related to cardiac contractions and relaxations. ECG measures various parameters that are specific to a subject and can assess the electrical and muscular functions of the subject's heart.

A pulse arrival time (PAT) refers to a time between an electrical activity of a human heart and an arrival of a pulse wave elsewhere in the human body, generally a periphery such as earlobe, fingers, and toes of a subject. The pulse arrival time may vary depending on various conditions and parameters. For example, personal variations of the subject such as arterial stiffness, tissue conductivity, variations in electrical and acoustic passages, and any other cardiovascular conditions of the subject may affect the pulse arrival time. In some cases, the pulse arrival time may be represented by and/or derived from a pulse transit time (PTT) and a pulse wave velocity.

Presently, continuous monitoring of blood pressure (BP) may be intrusive and non-user-friendly. The PAT measurement may be used to indirectly measure or estimate the continuous blood pressure by eliminating an intrusive and non-user-friendly blood pressure monitor such as a finger cuff and a tonometer. Further, there are situations in which a blood pressure monitor may not be used, for example, while driving or situations in which it is important to be not distracted.

Establishing a tight, reliable, and reproducible relationship between the blood pressure and the pulse arrival time is critical to provide a robust blood pressure estimation based on the pulse arrival time. Assessment of the blood pressure to the pulse arrival time relationship is challenging because the natural variation of the measured raw signals with respect to measurement noises is relatively small.

SUMMARY

According to one embodiment, a method for providing personalized health assessment of a subject includes: receiving a raw electrocardiography (ECG) signal of a subject from an ECG device and a raw blood pressure (BP) signal of the subject from a BP waveform detector; calculating a beat-to-beat ECG signal from the raw ECG signal; calculating a beat-to-beat BP signal from the raw BP signal; calculating a beat-to-beat pulse arrival time (PAT) signal that is measured as a time delay between the beat-to-beat ECG signal and the beat-to-beat BP signal; calculating an interpolated beat-to-beat PAT signal and an interpolated beat-to-beat BP signal by interpolating the beat-to-beat PAT signal and the beat-to-beat BP signal, respectively; assessing a subject-specific relationship between the interpolated beat-to-beat PAT signal and the interpolated beat-to-beat BP signal; and estimating a real-time blood pressure of the subject based on the subject-specific relationship.

According to another embodiment, an apparatus includes: a pulse arrival time (PAT) calculator configured to receive a raw electrocardiography (ECG) signal of a subject from an ECG device and a raw blood pressure (BP) signal of the subject from a BP waveform detector, calculate a beat-to-beat ECG signal, a beat-to-beat pulse wave signal, and calculate a beat-to-beat PAT signal from the beat-to-beat ECG signal and the beat-to-beat pulse wave signal; a BP calculator configured to receive the raw BP signal and calculate a beat-to-beat BP signal; an interpolator configured to interpolate the beat-to-beat PAT signal and the beat-to-beat BP signal and generate an interpolated beat-to-beat PAT signal and an interpolated beat-to-beat BP signal; and a BP-PAT relationship estimator configured to assess a subject-specific relationship between the interpolated beat-to-beat PAT signal and the interpolated beat-to-beat BP signal.

According to another embodiment, an apparatus includes: a pulse arrival time (PAT) calculator configured to receive a raw electrocardiography (ECG) signal of a subject from an ECG device and a raw pulse wave signal from a pulse wave detector and calculate a real-time pulse arrival time (PAT) signal from the raw ECG signal and the raw pulse wave signal; and a blood pressure (BP) estimator configured to receive the real-time PAT signal from the PAT calculator and estimate a real-time blood pressure of the subject based on a predetermined subject-specific relationship between a beat-to-beat PAT signal and a beat-to-beat BP signal without directly receiving the raw BP signal.

The above and other preferred features, including various novel details of implementation and combination of events, will now be more particularly described with reference to the accompanying figures and pointed out in the claims. It will be understood that the particular systems and methods described herein are shown by way of illustration only and not as limitations. As will be understood by those skilled in the art, the principles and features described herein may be employed in various and numerous embodiments without departing from the scope of the present disclosure.

BRIEF DESCRIPTION OF THE DRAWINGS

The accompanying drawings, which are included as part of the present specification, illustrate the presently preferred embodiment and together with the general description given above and the detailed description of the preferred embodiment given below serve to explain and teach the principles described herein.

FIG. 5 is a flowchart for assessing time delay between blood pressure and pulse arrival time, according to one embodiment.

Figure 1A:
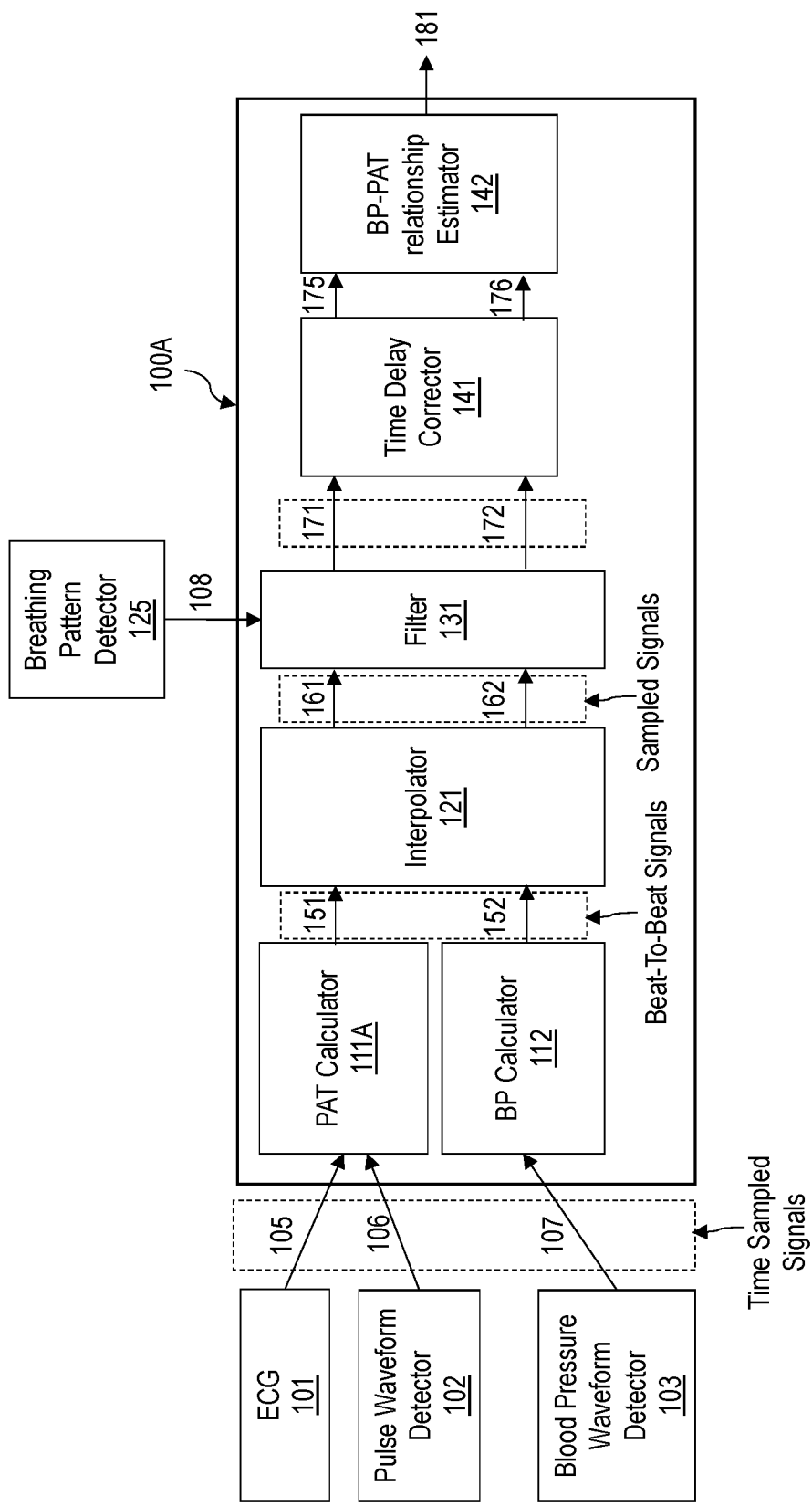
FIG. 1A shows a block diagram of an example system for assessing a time delay between a pulse arrival time and a blood pressure process according to one embodiment.

The figures are not necessarily drawn to scale and elements of similar structures or functions are generally represented by like reference numerals for illustrative purposes throughout the figures. The figures are only intended to facilitate the description of the various embodiments described herein. The figures do not describe every aspect of the teachings disclosed herein and do not limit the scope of the claims.

DETAILED DESCRIPTION

Each of the features and teachings disclosed herein can be utilized separately or in conjunction with other features and teachings to provide a system and method for accurately assessing personalized subject-specific relationship between a blood pressure and a pulse arrival time. Representative examples utilizing many of these additional features and teachings, both separately and in combination, are described in further detail with reference to the attached figures. This detailed description is merely intended to teach a person of skill in the art further details for practicing aspects of the present teachings and is not intended to limit the scope of the claims. Therefore, combinations of features disclosed above in the detailed description may not be necessary to practice the teachings in the broadest sense, and are instead taught merely to describe particularly representative examples of the present teachings.

In the description below, for purposes of explanation only, specific nomenclature is set forth to provide a thorough understanding of the present disclosure. However, it will be apparent to one skilled in the art that these specific details are not required to practice the teachings of the present disclosure.

Some portions of the detailed descriptions herein are presented in terms of algorithms and symbolic representations of operations on data bits within a computer memory. These algorithmic descriptions and representations are used by those skilled in the data processing arts to effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the below discussion, it is appreciated that throughout the description, discussions utilizing terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of an original disclosure, as well as for the purpose of restricting the claimed subject matter. It is also expressly noted that the dimensions and the shapes of the components shown in the figures are designed to help to understand how the present teachings are practiced, but not intended to limit the dimensions and the shapes shown in the examples.

The present disclosure provides a system and method for accurately assessing personalized subject-specific relationship between a blood pressure and a pulse arrival time that may vary depending on a subject. Once the relationship between the blood pressure and the pulse arrival time is accurately assessed, the relationship may be used to estimate the blood pressure of the subject non-invasively with improved reliability and accuracy. According to one embodiment, the subject-specific relationship between the blood pressure and the pulse arrival time may be represented as a time delay between a beat-to-beat blood pressure and a beat-to-beat pulse arrival time.

The present system and method provides signal processing and noise filtering techniques to obtain an accurate and reliable time delay specific to a subject. The present signal processing and noise filtering techniques overcomes challenges in measuring small changes of a blood pressure signal and a pulse arrival time that are sensitive to measurement noises.

According to one embodiment, the present system and method provides a robust, reliable, and reproducible estimation of the relationship between the blood pressure and the pulse arrival time. The estimated relationship between the blood pressure and the pulse arrival time may be expressed in terms of a time delay therebetween. The estimated relationship between PAT and BP may be used to estimate a blood pressure of a subject using ECG signals without a direct measurement of the subject's blood pressure using a blood pressure monitor. This eliminates an intervention and/or convenience so that the present system and method may be applied to situations in which direct measurement of the blood pressure is not appropriate such as an intensive care unit (ICU).

According to one embodiment, the present system and method provides a verification process and an application process. In the verification process, the relationship between the blood pressure and the pulse arrive time specific to a subject is verified, and a time delay specific to the subject is derived. In the application process, the blood pressure of the subject can be measured based the calculation of the pulse arrival time of the subject derived from the ECG and the subject-specific time delay that is obtained during the verification process for estimating the PAT-BP relationship of the subject.

FIG. 1A shows a block diagram of an example system for assessing a time delay between a pulse arrival time and a blood pressure process according to one embodiment. A system 100A includes a PAT calculator 111A, a BP calculator 112, an interpolator 121, a filter 131, a time delay corrector 141, and a PAT-BP relationship estimator 142.

The system 100A simultaneously receives electrophysiological signals such as ECG signals as well as blood pressure signals and/or pulse wave signals. For example, the system 100A simultaneously receives ECG signals 105 from an ECG device 101, pulse wave signals 106 from a pulse waveform detector 102, and blood pressure signals 107 from a blood pressure waveform detector 103. The PAT calculator 111A calculates beat-to-beat PAT signals 151 from the ECG signals 105 and the pulse wave signals 106, and the BP calculator 112 calculates beat-to-beat BP signal 152 from the blood pressure signals 107.

Figure 1B:
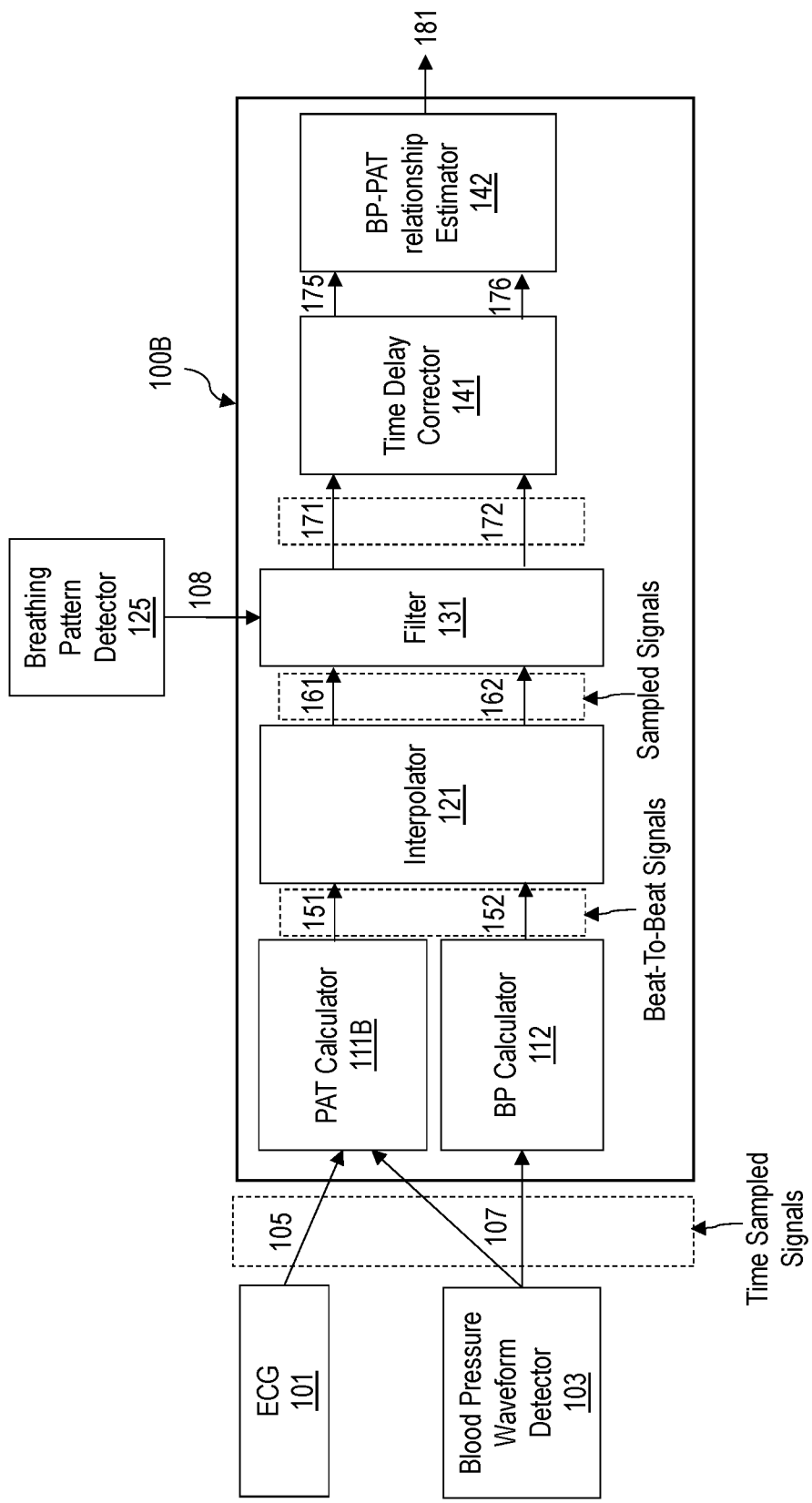
FIG. 1B shows a block diagram of an example system for assessing a time delay between a pulse arrival time and a blood pressure process according to another embodiment.

FIG. 1B shows a block diagram of an example system for assessing a time delay between a pulse arrival time and a blood pressure process according to another embodiment. A system 100B includes the PAT calculator 111B, the BP calculator 112, the interpolator 121, the filter 131, the time delay corrector 141, and the PAT-BP relationship estimator 142. The system 100B simultaneously receives the ECG signals 105 from the ECG device 101 and the blood pressure signals 107 from the blood pressure waveform detector 103. Unlike the PAT calculator 111A of the system 100A, the PAT calculator 111B calculates the beat-to-beat PAT signals 151 from the ECG signals 105 and the blood pressure signals 107. The BP calculator 112 calculates the beat-to-beat BP signal 152 from the blood pressure signals 107.

Examples of the pulse waveform detector 102 include, but are not limited to, a photoplethysmographic (PPG) pulse wave detector, a piezoelectric pulse wave detector, and an ultrasound transducer. An example of the blood pressure waveform detector 103 is a blood pressure monitor such as a finger cuff using the vascular unloading technique or tonometry. The system 100B of FIG. 1B receives the ECG signals 105 from the ECG device 101 and the blood pressure signals 107 from the blood pressure waveform detector 103, but this is only an example, In another example, the pulse wave signals 106 from the pulse waveform detector 102 may be optionally supplied to the system 100B. In this case, the PAT calculator 111B calculates the beat-to-beat PAT signals 151 from the ECG signals 105 and the blood pressure signals 107.

Referring to FIG. 1A and FIG. 1B, the PAT calculator 111B is configured to receive and sample the ECG signals 105 from the ECG device 101 and the blood pressure signals 107 from the blood pressure waveform detector 103 (and optionally the pulse wave signals 106 from the pulse waveform detector 102 as shown in FIG. 1A), and generate beat-to-beat PAT signals 151. Concurrently, the BP calculator 112 is configured to receive and sample the blood pressure signals 107 from the blood pressure waveform detector 103 and calculate the beat-to-beat BP signals 152.

According to one embodiment, the beat-to-beat PAT signals 151 can be calculated by determining a start of an electrical activity of the subject's heart from the ECG signals 105 and an arrival of a pulse wave from the PPG signals. For example, the start of the electrical activity of the heart can be identified by an R-peak that corresponds to a local maximum of the ECG signals. The arrival of the pulse wave can be identified as a point referred to an upstroke (e.g., the maximum of first derivative of the PPG signals) or the foot (e.g., the maximum of the second derivative of the signal) may be calculated from the PPG signals. In one embodiment, the beat-to-beat PAT signals 151 correspond to the difference between the R-peak of the ECG signals and the upstroke (or foot) of the pulse waveform of the PPG signals. It is understood that this is only an example, and other techniques for detecting the beat-to-beat PAT signals 151 may be used, for example, using an intersecting tangent method to identify the arrival of the pulse wave, without deviating from the scope of the present disclosure. The beat-to-beat BP signals 152 can be calculated as the systolic blood pressure (SBP) as the local maximum of the blood pressure waveform or alternatively, the diastolic blood pressure (DBP) as a local minimum.

Figure 2:
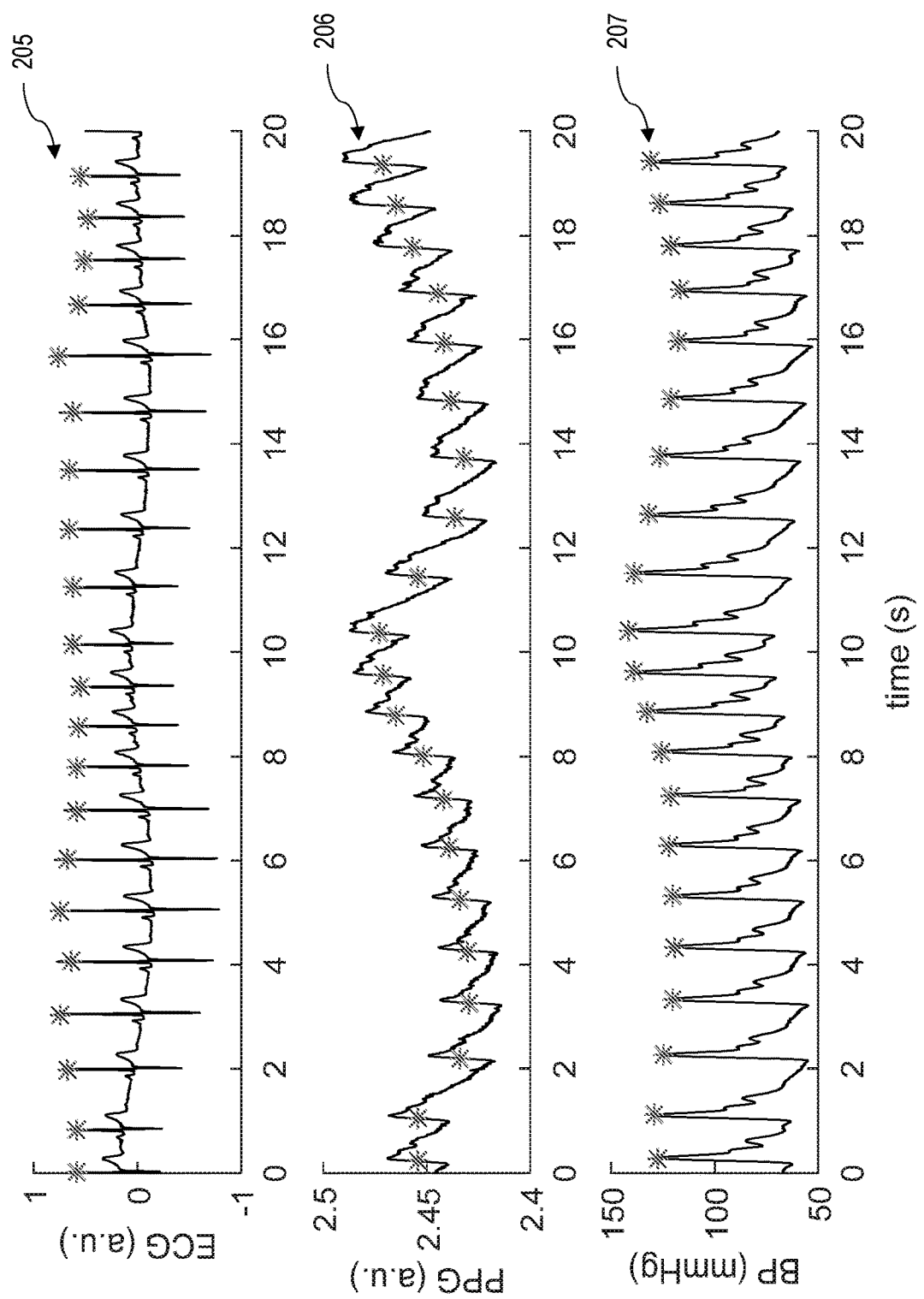
FIG. 2 shows examples of sampled signals representing electrical activity, pulse waveforms, and blood pressure waveforms according to one embodiment.

FIG. 2 shows examples of sampled signals representing electrical activity, pulse waveforms, and blood pressure waveforms according to one embodiment. The solid lines represent the raw signals received from the ECG device 101, the pulse waveform detector 102, and the blood pressure waveform detector 103 shown in FIG. 1A and FIG. 1B, and the stars represent the sampled signals 205, 206, and 207 that are sampled from the raw signals. For example, the sampled ECG signals 205 are obtained from the ECG signals 105 received from the ECG device 101, the sampled photoplethysmography (PPG) signals 206 are obtained from the pulse wave signals 106 from the pulse waveform detector 102, and the sampled BP signals 207 are obtained from the blood pressure signals 107 from the blood pressure waveform detector 103. The raw signals may be acquired during an interventional period to obtain reliable and stable raw signals of a subject, for example, during a paced breathing. The sampled signals 205, 206, and 207 can be used to derive cyclic variations associated with pulse arrival time signals that can be correlated to the subject's cardiac signals.

Referring back to FIG. 1A, the PAT calculator 111A calculates the beat-to-beat PAT signals 151 based on the sampled ECG signals 205 and the sampled pulse waveform detector signals 206 by determining a start of an electrical activity of the heart from the raw ECG signals 105 and an arrival of a pulse wave from the raw pulse wave signals 106. Alternatively, in the example of FIG. 1B, the PAT calculator 111B calculates the beat-to-beat PAT signals 151 based on the sampled ECG signals 205 and the sampled blood pressure signals 207. The BP calculator 112 calculates the beat-to-beat BP signals 152 by sampling the raw blood pressure signals 107 independently from the PAT calculator 111A or 111B. In some embodiments, the PAT calculator 111A or 111B and the BP calculator 112 are integrated in a single data calculator and perform sampling of the received raw signals in different data sampling channels.

Figure 3:
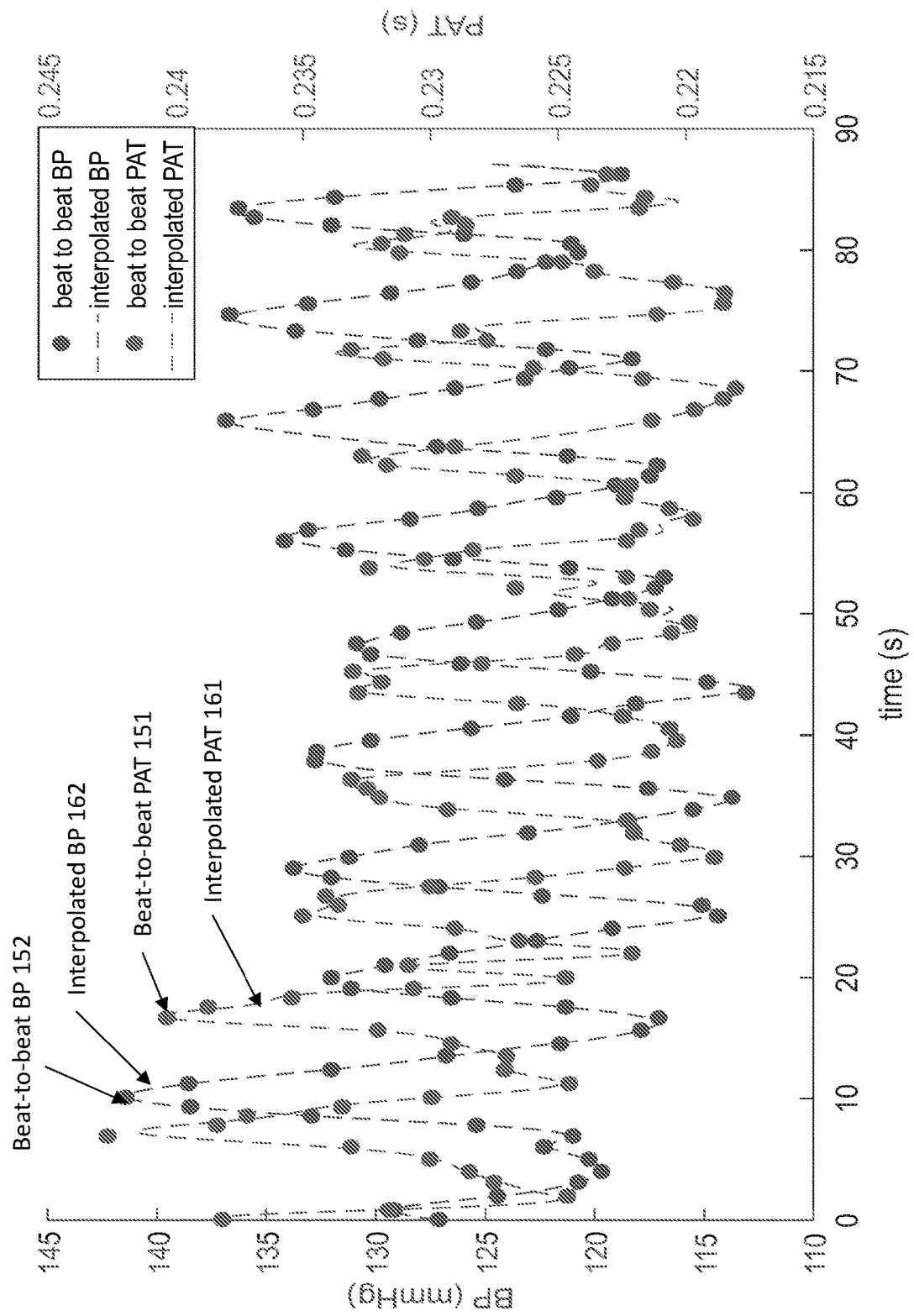
FIG. 3 shows an example of the beat-to-beat pulse arrival time and blood pressure and the corresponding interpolated signals.

The interpolator 121 receives the beat-to-beat PAT signals 151 from the PAT generator 111A or 111B and the beat-to-beat BP signals 152 from the BP generator 112 and generates interpolated beat-to-beat PAT signals 161 and interpolated beat-to-beat BP signals 162. Referring to FIG. 3, the beat-to-beat PAT signals 151 and the beat-to-beat BP signals 152 are represented by dots, and the interpolated beat-to-beat PAT signals 161 and the interpolated beat-to-beat BP signals 162 are represented by the dashed lines connecting the sampled signals of the beat-to-beat PAT signals 151 and the beat-to-beat BP signals 152. The beat-to-beat PAT signals 151 and the beat-to-beat BP signals 152 include at least a minimum number of signal samples of the raw ECG signals 105 and the raw blood pressure signals 107 to be able to correctly represent the corresponding beat-to-beat signals.

In general, beat-to-beat signals are not evenly spaced in time even if they occur every heartbeat. The interpolator 121 interpolates the unevenly spaced time sampled signals and output interpolated beat-to-beat signals that are time-equidistant. For example, linear, cubic, and spline (and other) interpolation techniques may be used. According to one embodiment, a sample frequency of the interpolated beat-to-beat signals may be substantial higher (e.g., 10 Hz or higher) than beat-to-beat time sample signals (e.g., approximately 1 Hz).

The filter 131 receives the interpolated PAT signals 161 and the interpolated BP signals 162 from the interpolator 121 and generates filtered PAT signals 171 and filtered BP signals 172. The filter 131 filters out noise and reduce noise components in the interpolated signals 161 and 162 to increase the signal-to-noise ratio of the interpolated signals According to one embodiment, the filter 131 receives optional breathing signals 108 from a breathing pattern detector 125. For example, the filter 131 may filter the input signals with fixed cut-off frequencies (characteristics). If a breathing rate of the subject is known, a better (e.g., subject-specific) filtering may be applied to further decrease the noise level in the input signals. According to one embodiment, the breathing rate of the subject may be obtained in one of the following ways: (1) paced breathing with a fixed and known breathing rate, (2) voluntary breathing (or paced but not fixed breathing rate), and (3) signals obtained one or more devices (e.g., the ECG device 101, the blood pressure waveform detector 103, the pulse waveform detector 102, a respiration belt, and a bio-impedance sensor).

The filtered PAT signals 171 and the filtered BP signals 172 are fed to the time delay corrector 141 and subsequently to the BP-PAT relationship estimator 142. The time delay corrector 141 calculates a subject-specific phase difference between the filtered PAT signals 171 and the filtered BP signals 172, herein referred to as a time-delay TD and provides time delay-corrected PAT and BP signals 175 and 176 to the BP-PAT relationship estimator 142. The time delay-corrected PAT and BP signals 175 and 176 are used by the BP-PAT relationship estimator 142 to provide relational information 181 between the filtered PAT signals 171 and the filtered BP signals 172. The relational information 181 may be later used to estimate a real-time BP of a subject without directly measuring the BP of the subject. Details of the use of the relational information 181 will be further explained with reference to FIG. 6 below.

According to one embodiment, the present system (e.g., 100A of FIG. 1A and 100B of FIG. 1B) can provide an estimation of a subject's blood pressure (BP) based on a pulse arrival time (PAT). Details of the blood pressure estimation will be discussed in further detail below with reference to FIGS. 5 and 6. To get a reliable estimation of the subject's blood pressure, it is essential to know the relationship between the blood pressure (BP) and pulse arrival time (PAT). The present blood pressure estimation technique is based on the assumption that there is a phase difference between the blood pressure and the pulse arrival time. The present system processes the raw signals, generates beat-to-beat signals, interpolate the beat-to-beat signals, removes high and low frequency noises on the interpolated signals, and accurately assess the phase difference between the blood pressure and the pulse arrival time.

Figure 4A:
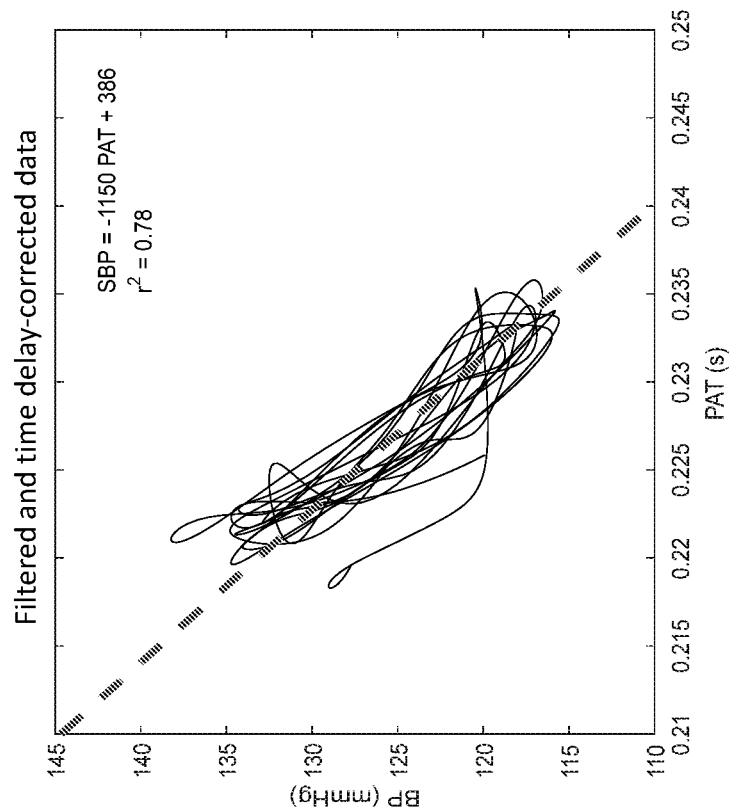
FIG. 4A shows an example of beat-to-beat and interpolated PAT and BP signals prior to applying filtering and time delay correction.
Figure 4B:
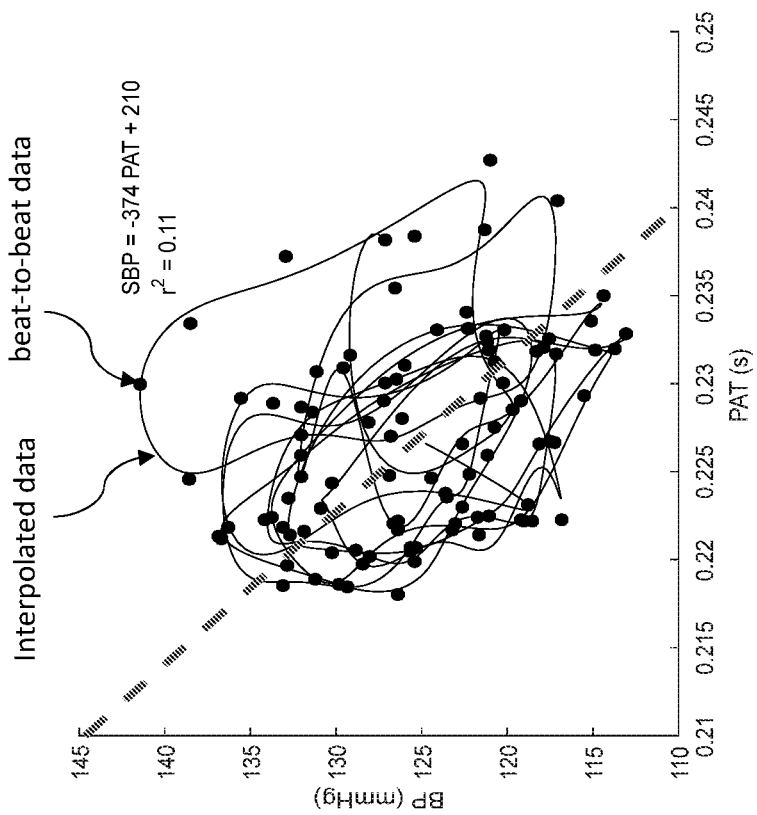
FIG. 4B shows an example of BP-PAT relationship after filtering and time delay correction according to one embodiment.

FIG. 4A shows an example of beat-to-beat and interpolated PAT and BP signals prior to applying filtering and time delay correction, and FIG. 4B shows an example of BP-PAT relationship after filtering and time delay correction according to one embodiment. The example of FIG. 4A illustrates a difficulty in identifying a relationship between the interpolated blood pressure and the interpolated pulse arrival time. A dotted line is shown as a comparative purpose to compare with the example of FIG. 4B. By filtering and applying time delay correction, the present system can derive better estimation of the relationship between the blood pressure and the pulse arrival time as shown in FIG. 4B. For example, a root-mean-square deviation $r^2$ of the example shown in FIG. 4A is 0.11 whereas it is 0.78 in the example shown in FIG. 4B. According to one embodiment, the relationship between the blood pressure and the pulse arrival time is a linear relationship represented by the slope of the dotted line. However, it is understood that the relationship between the blood pressure and the pulse arrival time is not limited to the linear relationship, and the present BP-PAT estimator provide the estimation in various other ways, for example, by looking up a lookup table. Once the PAT is accurately calculated by the cardiac signals of a subject, the blood pressure of the subject can be estimated by the present system without directly acquiring the blood pressure signals from the subject.

FIG. 5 is a flowchart for assessing time delay between blood pressure and pulse arrival time, according to one embodiment. ECG signals and continuous BP signals, and optionally pulse wave signals of a subject under test is received (step 501). According to one embodiment, an intervention to the subject under test is enforced to obtain detectable, reliable, and repeatable patterns on both blood pressure (BP) and pulse arrival time (PAT) signals to be processed. For example, the subject lies on a bed, and is asked to breath at a computer-controlled pace (e.g., sound guided pace). The ECG signals and the continuous BP signals received during a paced intervention may yield more accurate, reliable, and repeatable results. The ECG signals may be received from multiple leads of the ECG, and the continuous BP signals may be obtained using arterial line invasive BP signals or any less invasive BP measurement techniques such as vascular unloading technique or tonometry. The continuous BP signals may be acquired with tight synchronization and a sufficient time resolution and sampling rates (e.g., 50-1000 Hz). The continuous BP signals can be obtained invasively or by making use of, for example, a continuous arterial pressure device based on a vascular unloading technique. Optionally, pulse wave signals based on mechanical, optical, or other measurement techniques may be simultaneously obtained. The optionally provided pulse wave signals may yield more representative assessment of the PAT-to-BP relationship for the final application (as described in FIG. 6). For example, the pulse wave signals may be obtained with an infrared measuring PPG probe. PPG is used to estimate a volume change in the superficial tissue using infrared light.

The received ECG and continuous BP signals (and the optional pulse wave signals) are time sampled, and based on the sampled ECG and BP signals, an onset of electrical activity (or depolarization) of the ventricle (e.g., R peak, Q point, S point of the QRS complex) from the ECG, beat-to-beat BP signals (e.g., systolic BP or diastolic BP), and an arrival of a pulse waveform from the pulse wave signals or continuous BP signals are determined (step 502). In step 502, a systolic or diastolic blood pressure from the continuous BP signals is obtained as well. For example, the arrival of the pulse waveform may be calculated either directly from the pulse waveform detector or the BP waveform detector and the ECG waveform detector. Next, a pulse arrival time (PAT) is calculated as a time delay from the onset of an electrical activity of the ventricle to the arrival of the pulse wave, and beat-to-beat PAT and BP signals are calculated (step 503). For example, the PAT may be calculated by determining the arrival time between the ECG and PPG signals (e.g., an R-peak of the ECG signals to an upstroke of the PPG signals), and a systolic blood pressure is obtained as the local maximum of the pressure wave signals (or a diastolic blood pressure is obtained as the local minimum of the pressure wave signals). It is noted that the calculated pulse arrival time and the BP signals obtained in step 502 may be obtained on a beat-to-beat basis. In this case, the raw signals may be unevenly sampled with a relatively high sample interval that is equal to the heart cycle duration.

The PAT signals and the BP signals are interpolated to get evenly spaced signal samples, and the interpolated signals are filtered (step 504). For example, a spline interpolation is used to interpolate the unevenly sampled signals, and the interpolation may effectively up-sample the input signals to generate the corresponding signals with a finer time resolution. Using the interpolated and filtered PAT and BP signals, a phase difference (i.e., time delay) is determined between the PAT and BP signals (step 505). Such a task may require signal processing techniques, including band-pass filtering to remove high and low frequency noises, normalization of the signals and cross-correlation techniques that exploit the repetitive nature of the intervention to anchor the time delay between the PAT and BP signals. The phase difference correction and obtain the BP-PAT relationship is applied (step 506). The phase difference may be obtained using cross correlation between the interpolated PAT and BP signals to compute a time delay between the signals. The time delay between the BP and PAT signals provides personalized assessment of the subject under test. For example, it is tested whether the BP and PAT signals have a linear relationship, for example, the root-mean-square deviation of the signals is smaller than a threshold value, and the linear relationship is considered as a personalized health parameter that is unique for the subject under test. Linear regression technique may be applied to obtain the BP-PAT relationship as shown in FIG. 4B.

According to one embodiment, multiple interventions may be used to obtain baseline assessment of the subject under test. The present system and method works with cyclical BP-changing interventions such as paced breathing including other interventions such as raising your arm in a particular pattern, standing and siting at time intervals, etc. As an additional step, the intervention may be used periodically, and the periodicity of the cyclic intervention may be used to improve the signal processing. The pulse wave signals can be obtained using one or more of PPG signals, piezo displacement pulse wave signals, sound-based pulse wave signals, radar-based pulse wave signals, and other pulse wave signals that may be obtained with various sensory technologies. It is noted that the present system and method is not limited for a use of non-invasive blood pressure measurement but can also be used to characterize arterial stiffness or other cardiovascular health parameters of the subject without deviating from the scope of the present disclosure. For example, the slope of the BP-PAT relationship (e.g., BP=−slope*PAT+offset) may represent arterial stiffness of the subject. A lower slope indicates less stiff artery, and it can be used as a health indicator of the subject.

According to one embodiment, the estimation of the blood pressure is not restricted to be used with PAT only, other beat-to-beat parameters, including a heart rate and a pulse transit time can be used as well. The estimated time delay may be used as an input for other health parameters or used as a health parameter on its own. Other method can be used to obtain the phase difference and the time delay between the PAT and BP signals. In addition, an instantaneous phase difference may be obtained by applying a transformation technique, for example, Hilbert transform, calculating complex autocorrelation, and calculating an instantaneous frequency from the complex autocorrelation. According to one embodiment, an alternative technique that allows correction of the phase difference with a finer time resolution than the heart cycle duration can be used.

Figure 6:
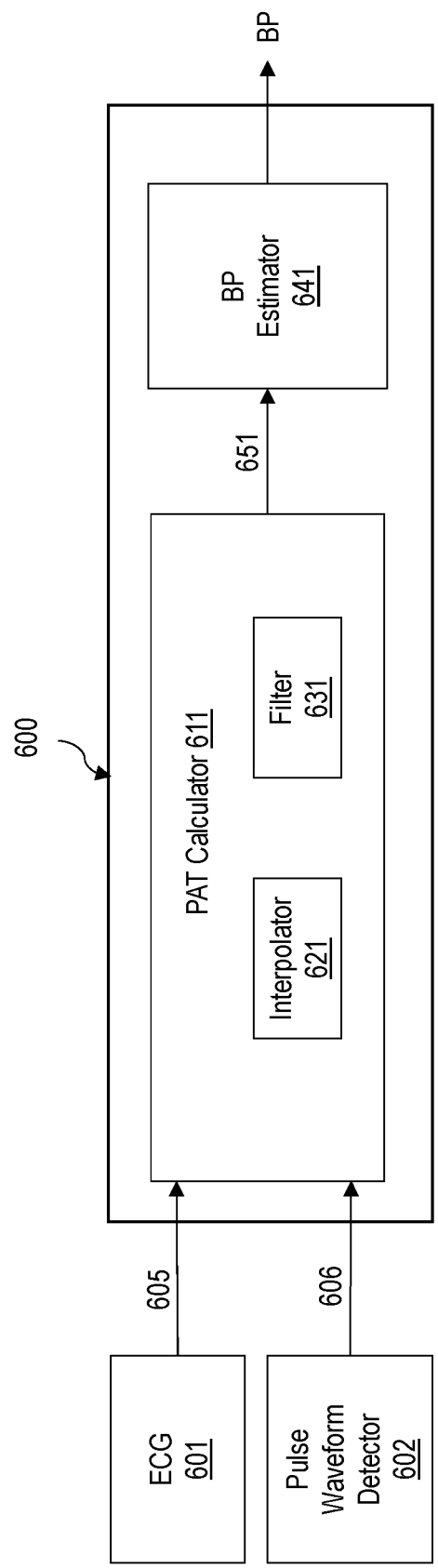
FIG. 6 shows a block diagram of an example system for estimating a blood pressure according to one embodiment.

FIG. 6 shows a block diagram of an example system for estimating a blood pressure according to one embodiment. A system 600 includes a PAT calculator 611 and a blood pressure (BP) estimator 641, and optionally includes an interpolator 621 and a filter 631. The PAT calculator 611 is configured to receive and sample ECG signals 605 from an ECG device 601 and pulse wave signals 606 from a pulse waveform detector 602, and generate beat-to-beat PAT signals 651.

The interpolator 621 generates interpolated PAT signals. The filter 631 receives the interpolated PAT signals from the interpolator 621, filters the interpolated PAT signals. and generates filtered PAT signals 651. The filter 631 filters out noise and reduce noise components in the interpolated PAT signals to increase the signal-to-noise ratio. The interpolator 621 and the filter 631 may be omitted in some embodiments. The BP estimator 641 receives the PAT signals 651 and generates an estimated blood pressure BP based on the relational information between the PAT signals and the BP signals specific to the subject (e.g., 181 shown in FIG. 1A and FIG. 1B). According to one embodiment, the BP estimator 641 to generate the estimated blood pressure BP in real time based on the ECG signals 605 and the pulse wave signals 606 without requiring a direct measurement of blood pressure signals. In some embodiment, the estimator 641 may receive different input signals that are indicative of another health parameter of the subject and provide a health parameter as an output that may or may not include the BP.

According to one embodiment, a method for providing personalized health assessment of a subject includes: receiving a raw electrocardiography (ECG) signal of a subject from an ECG device and a raw blood pressure (BP) signal of the subject from a BP waveform detector; calculating a beat-to-beat ECG signal from the raw ECG signal; calculating a beat-to-beat BP signal from the raw BP signal; calculating a beat-to-beat pulse arrival time (PAT) signal that is measured as a time delay between the beat-to-beat ECG signal and the beat-to-beat BP signal; calculating an interpolated beat-to-beat PAT signal and an interpolated beat-to-beat BP signal by interpolating the beat-to-beat PAT signal and the beat-to-beat BP signal, respectively; assessing a subject-specific relationship between the interpolated beat-to-beat PAT signal and the interpolated beat-to-beat BP signal; and estimating a real-time blood pressure of the subject based on the subject-specific relationship.

The method may further include filtering the interpolated beat-to-beat PAT signal and the interpolated beat-to-beat BP signal using a band-pass filter.

The method may further include: receiving a breathing pattern of the subject; and filtering out a noise from the breathing pattern to generate a phase difference between the interpolated beat-to-beat PAT signal and the interpolated beat-to-beat BP signal.

The subject-specific relationship may be obtained based on a relationship between the interpolated beat-to-beat PAT signal and the interpolated beat-to-beat BP signal.

The raw ECG signal and raw the BP signal may be received during a paced breathing period.

The method may further include: receiving a raw pulse wave signal from a pulse wave detector; and calculating a beat-to-beat pulse arrival signal from the raw pulse wave signal. The beat-to-beat PAT signal may be calculated using the beat-to-beat pulse arrival signal and a start of an electrical activity using the raw ECG signal.

The start of the electrical activity may be calculated using an R-peak, a Q point, or an S point of the raw ECG signal.

The method may further include: calculating a real-time pulse arrival time (PAT) signal; estimating the real-time blood pressure of the subject based on the real-time PAT signal and the subject-specific relationship without directly receiving the raw BP signal.

The time delay may be used as a personalized health assessment parameter of the subject.

According to another embodiment, an apparatus includes: a pulse arrival time (PAT) calculator configured to receive a raw electrocardiography (ECG) signal of a subject from an ECG device and a raw blood pressure (BP) signal of the subject from a BP waveform detector, calculate a beat-to-beat ECG signal, a beat-to-beat pulse wave signal, and calculate a beat-to-beat PAT signal from the beat-to-beat ECG signal and the beat-to-beat pulse wave signal; a BP calculator configured to receive the raw BP signal and calculate a beat-to-beat BP signal; an interpolator configured to interpolate the beat-to-beat PAT signal and the beat-to-beat BP signal and generate an interpolated beat-to-beat PAT signal and an interpolated beat-to-beat BP signal; and a BP-PAT relationship estimator configured to assess a subject-specific relationship between the interpolated beat-to-beat PAT signal and the interpolated beat-to-beat BP signal.

The apparatus may further include a band-pass filter configured to filter the interpolated beat-to-beat PAT signal and the interpolated beat-to-beat BP signal.

The band-pass filter may be configured to receive a breathing pattern of the subject during an intervention and filter out a noise from the breathing pattern to generate a phase difference between the interpolated beat-to-beat PAT signal and the interpolated beat-to-beat BP signal.

The PAT calculator may further be configured to: receive a raw pulse wave signal from a pulse wave detector; and calculate a beat-to-beat pulse wave signal from the raw pulse wave signal. The beat-to-beat PAT signal may be calculated using the beat-to-beat pulse wave signal and the beat-to-beat ECG signal.

The pulse wave detector may be one of a piezoelectric pulse wave detector and an ultrasound transducer.

The BP waveform detector may be a finger cuff or a tonometer.

The raw ECG signal and raw the BP signal may be received during a paced breathing period.

The subject may be guided to breath at a computer-controlled pace during the paced breathing period.

The beat-to-beat ECG signal may be measured based on an onset of an electrical activity that is calculated using an R-peak, a Q point, or an S point of the raw ECG signal.

The subject-specific relationship may be obtained based on a linear relationship between the interpolated beat-to-beat PAT signal and the interpolated beat-to-beat BP signal.

According to another embodiment, an apparatus includes: a pulse arrival time (PAT) calculator configured to receive a raw electrocardiography (ECG) signal of a subject from an ECG device and a raw pulse wave signal from a pulse wave detector and calculate a real-time pulse arrival time (PAT) signal from the raw ECG signal and the raw pulse wave signal; and a blood pressure (BP) estimator configured to receive the real-time PAT signal from the PAT calculator and estimate a real-time blood pressure of the subject based on a predetermined subject-specific relationship between a beat-to-beat PAT signal and a beat-to-beat BP signal without directly receiving the raw BP signal.

The above example embodiments have been described hereinabove to illustrate various embodiments of implementing a system and method for accurately assessing personalized subject-specific relationship between a blood pressure and a pulse arrival time. Various modifications and departures from the disclosed example embodiments will occur to those having ordinary skill in the art. The subject matter that is intended to be within the scope of the invention is set forth in the following claims.

What is claimed is:

1. A method comprising:
   receiving a raw electrocardiography (ECG) signal of a subject from an ECG device and a raw blood pressure (BP) signal of the subject from a BP waveform detector;
   calculating a beat-to-beat ECG signal from the raw ECG signal;
   calculating a beat-to-beat BP signal from the raw BP signal;
   calculating a beat-to-beat pulse arrival time (PAT) signal that is measured as a time delay between the beat-to-beat ECG signal and the beat-to-beat BP signal;
   calculating an interpolated beat-to-beat PAT signal and an interpolated beat-to-beat BP signal by interpolating the beat-to-beat PAT signal and the beat-to-beat BP signal, respectively;
   calculating a subject-specific phase difference between the interpolated beat-to-beat PAT signal and the interpolated beat-to-beat BP signal; and
   estimating a real-time blood pressure of the subject based on the subject-specific relationship.

2. The method of claim 1, further comprising filtering the interpolated beat-to-beat PAT signal and the interpolated beat-to-beat BP signal using a band-pass filter.

3. The method of claim 2, further comprising:
   receiving a breathing pattern of the subject; and
   filtering out a noise from the breathing pattern to generate a phase difference between the interpolated beat-to-beat PAT signal and the interpolated beat-to-beat BP signal.

4. The method of claim 1, wherein the subject-specific relationship is obtained based on a relationship between the interpolated beat-to-beat PAT signal and the interpolated beat-to-beat BP signal.

5. The method of claim 1, wherein the raw ECG signal and raw the BP signal are received during a paced breathing period.

6. The method of claim 1, further comprising:
   receiving a raw pulse wave signal from a pulse wave detector; and
   calculating a beat-to-beat pulse arrival signal from the raw pulse wave signal,
   wherein the beat-to-beat PAT signal is calculated using the beat-to-beat pulse arrival signal and a start of an electrical activity using the raw ECG signal.

7. The method of claim 6, wherein the start of the electrical activity is calculated using an R-peak, a Q point, or an S point of the raw ECG signal.

8. The method of claim 1, further comprising:
   calculating a real-time pulse arrival time (PAT) signal; and estimating the real-time blood pressure of the subject based on the real-time PAT signal and the subject-specific relationship without directly receiving the raw BP signal.

9. The method of claim 1, wherein the time delay is used as a personalized health assessment parameter of the subject.

10. An apparatus comprising:
a pulse arrival time (PAT) calculator configured to receive a raw electrocardiography (ECG) signal of a subject from an ECG device and a raw blood pressure (BP) signal of the subject from a BP waveform detector, calculate a beat-to-beat ECG signal, a beat-to-beat pulse wave signal, and calculate a beat-to-beat PAT signal that is measured as a time delay between the beat-to-beat ECG signal and the beat-to-beat pulse wave signal;
a BP calculator configured to receive the raw BP signal and calculate a beat-to-beat BP signal;
an interpolator configured to interpolate the beat-to-beat PAT signal and the beat-to-beat BP signal and generate an interpolated beat-to-beat PAT signal and an interpolated beat-to-beat BP signal;
a time delay corrector configured to calculate a subject-specific phase difference between the interpolated beat-to-beat PAT signal and the interpolated beat-to-beat BP signal; and
a BP-PAT relationship estimator configured to assess a subject-specific relationship between the interpolated beat-to-beat PAT signal and the interpolated beat-to-beat BP signal.

11. The apparatus of claim 10, further comprises a band-pass filter configured to filter the interpolated beat-to-beat PAT signal and the interpolated beat-to-beat BP signal.

12. The apparatus of claim 11, wherein the band-pass filter is configured to receive a breathing pattern of the subject during an intervention and filter out a noise from the breathing pattern to generate a phase difference between the interpolated beat-to-beat PAT signal and the interpolated beat-to-beat BP signal.

13. The apparatus of claim 10, wherein the PAT calculator is further configured to:
receive a raw pulse wave signal from a pulse wave detector; and
calculate a beat-to-beat pulse wave signal from the raw pulse wave signal,
wherein the beat-to-beat PAT signal is calculated using the beat-to-beat pulse wave signal and the beat-to-beat ECG signal.

14. The apparatus of claim 13, wherein the pulse wave detector is one of a piezoelectric pulse wave detector and an ultrasound transducer.

15. The apparatus of claim 10, wherein the BP waveform detector is a finger cuff or a tonometer.

16. The apparatus of claim 10, wherein the raw ECG signal and raw the BP signal are received during a paced breathing period.

17. The apparatus of claim 16, wherein the subject is guided to breath at a computer-controlled pace during the paced breathing period.

18. The apparatus of claim 10, wherein the beat-to-beat ECG signal is measured based on an onset of an electrical activity that is calculated using an R-peak, a Q point, or an S point of the raw ECG signal.

19. The apparatus of claim 10, wherein the subject-specific relationship is obtained based on a linear relationship between the interpolated beat-to-beat PAT signal and the interpolated beat-to-beat BP signal.

20. An apparatus comprising:
a pulse arrival time (PAT) calculator configured to receive a raw electrocardiography (ECG) signal of a subject from an ECG device and a raw pulse wave signal from a pulse wave detector and calculate a real-time pulse arrival time (PAT) signal that is measured as a time delay between the raw ECG signal and the raw pulse wave signal; and
a blood pressure (BP) estimator configured to receive the real-time PAT signal from the PAT calculator calculate a subject-specific phase difference between the interpolated beat-to-beat PAT signal and the interpolated beat-to-beat BP signal, and estimate a real-time blood pressure of the subject based on a predetermined subject-specific relationship between a beat-to-beat PAT signal and a beat-to-beat BP signal without directly receiving the raw BP signal.

* * * * *

UNITED STATES PATENT AND TRADEMARK OFFICE
CERTIFICATE OF CORRECTION

| | | |
|---|---|---|
| PATENT NO. | : 11,529,060 B2 | |
| APPLICATION NO. | : 16/530919 | |
| DATED | : December 20, 2022 | |
| INVENTOR(S) | : Evelien Hermeling and Eva Wentink | |

It is certified that error appears in the above-identified patent and that said Letters Patent is hereby corrected as shown below:

On the Title Page

Item (73) should read:
Assignee: Samsung Electronics Co., Ltd.

Signed and Sealed this
Eighteenth Day of July, 2023

Katherine Kelly Vidal
*Director of the United States Patent and Trademark Office*